Aug. 7, 1928. Re. 17,059

G. N. HEIN

ADJUSTABLE PACKING FOR HYPODERMIC SYRINGES

Original Filed Aug. 26, 1924

INVENTOR.
George N. Hein.

BY
Townsend, Loftus & Attett
ATTORNEYS.

Reissued Aug. 7, 1928. Re. 17,059

UNITED STATES PATENT OFFICE.

GEORGE N. HEIN, OF SAN FRANCISCO, CALIFORNIA, ASSIGNOR TO NEUTYPE INSTRUMENT COMPANY, OF SAN FRANCISCO, CALIFORNIA, A CORPORATION OF CALIFORNIA.

ADJUSTABLE PACKING FOR HYPODERMIC SYRINGES.

Original No. 1,561,854, dated November 17, 1925, Serial No. 734,208, filed August 26, 1924. Application for reissue filed November 16, 1927. Serial No. 233,696.

This invention relates to means for adjusting the packing of piston in a hypodermic syringe without removing the piston from within the barrel.

The objects of the invention are, among others, to provide means whereby an elastic piston is capable of adjustment so that a snug fit can be had between the periphery of the same and the barrel wall; to provide a construction whereby a snugly fitting piston is adapted for readily releasing from the barrel wall should the same adhere or stick thereto; to provide a structure wherein the end wall of the barrel and one portion of the packing retaining head are fashioned to afford co-acting surfaces, the latter when in engagement reducing to a minimum the relative axial movement between the packing retaining head and the barrel and wall, enabling the desired adjustment of the packing to be obtained on a relative rotary movement being imparted to the piston and barrel.

With the above mentioned and other objects in view, the invention consists in the novel construction and combination of parts hereinafter described, illustrated in the accompanying drawings, and set forth in the claims hereto appended, it being understood that various changes in the form, proportion, size and minor details of construction within the scope of the claims may be resorted to without departing from the spirit or sacrificing any of the advantages of the invention.

To more fully comprehend the invention, reference is directed to the accompanying drawings, wherein.

Figure 1:
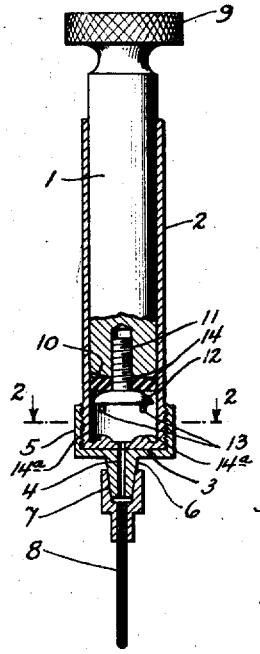
Fig. 1 is a view partly in vertical section of the preferred embodiment of my construction.

In the drawings, wherein like characters of reference designate corresponding parts, 1 indicates a cylindrical piston mounted for reciprocation and axial rotation within a tubular barrel 2, the same being a conventional hypodermic syringe barrel. The barrel is formed with an end wall 3 having a discharge opening 4, and in the embodiment illustrated there is detachably secured at the end 3 of the barrel provided with the outlet a shell or cap 5 having a tubular discharge nozzle 6 registering with the outlet 4. The disclosure is illustrated with the base 7 of a hypodermic needle 8 positioned on the discharge nozzle 6. One end of the piston 1 is provided with any suitable form of finger grip 9, and the other end is domed or rounded as at 10, and threaded thereinto is the stem 11 of a headed packing retaining member 12, the latter being formed with a radial curved surface disposed oppositely to the dome or curved surface 10 of the piston end.

Figure 2:
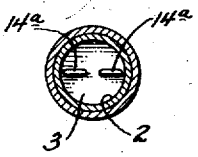
Fig. 2 is a transverse sectional view on line 2—2 of Fig. 1.

In the embodiment illustrated in Fig. 1, the retaining head or member 12 has extended from its outer face projections 13 which are adapted for contact with projections 14[a], and the inner surface of the end wall 3 clearly illustrated in Figs. 1 and 2, and mounted between the member 12 in the domed end 10 of the piston 1, is an elastic packing or washer 14 of a size, when not expanded, to lightly contact with the inner wall surface of the barrel 2, and the expansion of which, due to its elasticity, being controlled by the relative adjustment of the member 12 and the end 10. The adjustment stated above may be accomplished without withdrawing the piston from the barrel by first forcing the piston fully within the barrel until the projections 13 engage with projections 14, thereafter relative axial movement in opposite directions being imparted to the piston and barrel, causing greater or less tension to be placed on the packing; expanding and contracting the same as desired.

Figure 3:
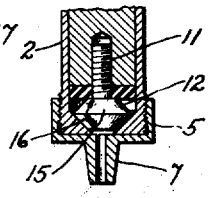
Fig. 3 is a vertical section of a barrel and syringe illustrating a modified form of packing retaining head.

Fig. 3 illustrates the outer face of the retaining member 12, being fashioned in substantially conical formation as at 15 to frictionally engage corresponding surface 16 formed on the inner face of the end wall of the barrel 2.

Figure 4:
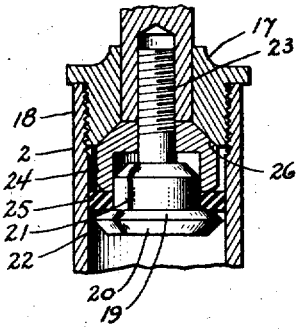
Fig. 4 is a further modified form of retaining head and adjusting mechanism.
Figure 5:
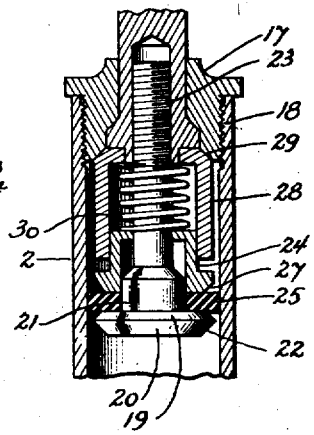
Fig. 5 is a still further modified form, illustrating spring means associated with the stem of the retaining head.

In the modifications illustrated in Figs. 4 and 5, the piston disclosed is of reduced diameter to that illustrated in Fig. 1, and is guided in an opening disposed centrally of a closure member 17 threaded to the upper end of the barrel 2 as at 18.

In these respective modifications, the headed packing retaining member is formed with the beveled peripheral walls 19 and 20, and a shell guiding boss 21 is disposed between the head 22 and the threaded stem 23. The boss 21 forms a guide for a thimble 24 loosely mounted on the stem 23 and between the lower peripheral edge of which and the upper surface of the head 22 is mounted an elastic packing washer 25.

In Fig. 4, the upper portion of the thimble 23 is provided with a friction surface 26 to engage on the upward movement of the piston within the barrel 2 with the beveled surface of the closure member 17 and transmit the resistance through the packing 25 to the head 22 to cause said head to move with the barrel when relative axial rotation in opposite directions is imparted to the piston and barrel.

In Fig. 5, the thimble 24 is formed with an annular seat 27 on which rests the lower end of a sleeve 28 surrounding the stem 23, and in this case the upper end of the sleeve 28 is beveled as at 29 to provide a surface for frictionally engaging the beveled surface of the member 17 when the piston is drawn its full length upwardly in the barrel. In this construction, a spring 30 coiled about the threaded stem 23 bears against the upper end of the thimble 24 and normally retains the same snugly in contact with the elastic packing 25.

It will be observed that the disclosure illustrated in Figs. 1, 2, and 3 of the drawings is adjustable in the syringe only after the piston has completed its full discharge stroke, and the disclosure in Figs. 4 and 5 enables the adjustment of the elastic packing when the piston is at either end of its stroke.

Figure 6:
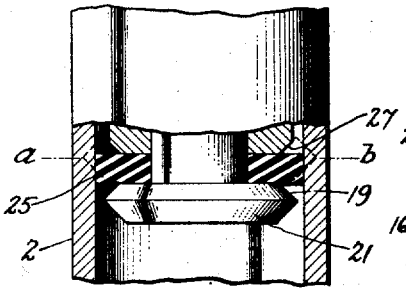
Fig. 6 shows a sectional view of the packing member and related parts, illustrating the position of the packing member when the piston is thrust inwardly to discharge the contents of the syringe.

The position of the packing member in actual use is illustrated in Fig. 6. Due to the inclined or beveled surface 27 on the piston, the packing member will, when the piston is moved inwardly to discharge the contents of the syringe, be deflected so as to present an edged surface with minimum contact area between the packing member and the barrel. Such a minimum contact area will greatly reduce the friction between the parts, and permit the syringe to be operated with great ease and facility. Furthermore, this deflection of the packing member will, in addition to reducing the friction, cause an expansion of the circumferential area of the packing member on a line *a—b* extending from one lower corner to the other. This expansion will cause an increased radial pressure to be exerted upon the walls of the barrel, thereby effecting a perfect sliding seal between the packing member and the barrel. The beveled surface 27 affords a seat for the rear face of the packing member when it is thus deflected, and is such as to prevent the packing member from being deflected so far as to destroy the minimum contact area and increased radial pressure.

Where the rear face of the retaining member is beveled or curved as indicated at 19, a similar action, in the reverse direction, occurs to the packing member when the piston is drawn outwardly to fill the syringe.

Having thus described my invention, what I claim and desire to protect by Letters Patent of the United States is:

1. A hypodermic syringe including a barrel substantially closed at one end providing a discharge port, a piston mounted for reciprocation and axial rotation therein, a packing retaining head threaded into the end of the piston, said piston and retaining head being provided with opposing walls affording a chamber within which a packing is positioned, said walls extending in opposite directions outwardly from each other, an elastic disc washer packing positioned within the chamber with its inner portion held between the piston end and retaining head walls and with this periphery lying parallel to the barrel surface and free to flex between the outer portions of the piston and retaining head walls, and means for affording a resistance to the head to retain the same substantially stationary on the imparting of relative rotary movement between the barrel and piston whereby the pressure of the packing against the barrel wall may be varied.

2. A hypodermic syringe including a barrel provided with a substantially closed end formed with recesses on its inner surface and provided with a discharge port, a piston mounted for reciprocation and axial rotation therein, a packing retaining head threaded into the end of the piston, said piston and retaining head being provided with co-operating surfaces curved from the center radially in opposite directions, a relatively thin elastic disc washer packing positioned between the piston end and retaining head with its periphery lying parallel to the barrel surface, said retaining head on its end provided with projections for reception in the recesses in the barrel end wall to hold the same substantially stationary on the imparting of relative rotary movement between the barrel and piston whereby the pressure of the packing against the wall barrel may be varied.

3. A piston for hypodermic syringes including a stem, a head carried by one end thereof and movable to and from the stem end on the axial rotation of the stem, opposing surfaces of said stem end and head being formed to recede outwardly from each other, and an elastic packing disc disposed with its center held between the stem end and head with its peripheral edge unsupported and free to flex between the walls of the stem and head and with its peripheral surface lying at right angles to the opposite faces of the disc.

4. A hypodermic syringe comprising a barrel, a piston therein, a normally flat, relatively thin, square-edged, elastic packing member on said piston, and a retaining member for said elastic packing member, said piston having a surface adjacent the packing member formed with beveled corners, whereby when the piston is moved inwardly the packing member will be deflected and present an edge contact against the barrel, minimizing thereby the friction between the packing member and barrel, and increasing the pressure of the packing member on the barrel in a radial direction.

5. A hypodermic syringe comprising a barrel, a piston therein, a normally flat, relatively thin, square-edged, elastic packing member on the piston, a retaining member for the elastic packing member, said piston and retaining member being each provided with a beveled surface adjacent the packing member, whereby, when the piston is moved in either direction, the packing member will be deflected and present an edge contact against the wall of the barrel, minimizing thereby the friction between the packing member on the barrel, and increasing the pressure of the packing member on the barrel in a radial direction.

GEORGE N. HEIN.